United States Patent [19]

Rampignon

[11] 4,248,710

[45] Feb. 3, 1981

[54] APPARATUS FOR THE PURIFICATION OF WATER POSSESSING SOLVENT WASTE CONTENT

[76] Inventor: Jack Rampignon, 116 rue Pierre Valdo, Lyons 5eme, France

[21] Appl. No.: 10,241

[22] Filed: Feb. 8, 1979

[30] Foreign Application Priority Data

Mar. 31, 1978 [FR] France ................................ 78 10350

[51] Int. Cl.³ ............................................. B03D 3/00
[52] U.S. Cl. .................................... 210/104; 210/259; 210/313; 55/160; 55/218
[58] Field of Search ................. 210/86, 104, 259, 303, 210/311, 313; 55/210, 218, 159, 160

[56] References Cited

U.S. PATENT DOCUMENTS

| | | | |
|---|---|---|---|
| 730,356 | 6/1903 | Emond | 210/311 X |
| 3,291,562 | 12/1966 | Anderson | 210/259 X |
| 3,429,148 | 2/1969 | Worthington | 210/259 X |
| 4,089,662 | 5/1978 | Williams | 210/104 X |
| 4,092,846 | 6/1978 | Jeffray et al. | 55/218 X |

*Primary Examiner*—John Adee
*Attorney, Agent, or Firm*—Remy J. VanOphem

[57] ABSTRACT

An apparatus for providing permanent decantation and separation of solvents miscible or nonmiscible in water, which are nonconductive and are absorbed by activated carbon. Water containing the solvent is passed through a decanter separator for separating nonmiscible solvent from the water solution. After flowing through the decanter separator, the solvent saturated water is gravity fed to a filter element of microscopic porosity for absorbing solvent dissolved in the water. The water is then passed through a detection cell which is connected downstream of the filter element. The detection cell includes a solvent vapor detection head connected to an electronic circuit controlling alarms. Air is bubbled through the water and the detection cell to accelerate evaporation of the solvent dissolved in the water. If any solvent is present in the air, the detection head activates visual and sound alarms. Finally, the water discharged from the detection cell is then passed through an auxiliary filtering element of microscopic porosity before the water is discharged into the sewer. The apparatus provides a saving of solvent and prevents the flow of solvent into the sewer.

11 Claims, 8 Drawing Figures

APPARATUS FOR THE PURIFICATION OF WATER POSSESSING SOLVENT WASTE CONTENT

BACKGROUND OF THE INVENTION

1. Field of the Invention

The invention pertains to an apparatus for the purification of water possessing solvent waste content.

2. Description of the Prior Art

In particular the invention applies to water containing perchlorethylene which is discharged from clothing degreasing machines. At the conclusion of the cleaning cycle, these machines regenerate the perchlorethylene through distillation resulting in the elimination of water and contaminants present in solution in the perchlorethylene.

The first stage of the distillation consists of the conversion of a water-solvent azeotrope to a pure state. The dissociation of the solvent molecules from the water molecules at the azeotrope stage is made in the condenser, and the separation, caused by the differences in density, occurs in a separator built in the machine. The solvent saturated water recovered in the separator is discharged directly into the sewer.

This results in contamination of sewers and of waste treatment installations, and creates a poisoning hazard for the installation personnel.

Inhalation of perchlorethylene vapors can induce, relative to time of exposure, the following disorders: headaches, vomiting, temporary loss of eyesight, nervous system disorders and hepatitis.

The purpose of the invention is to produce an apparatus which can purify water possessing solvent content, so that the waste water discharged into the sewers does not include the aforesaid hazards.

SUMMARY OF THE INVENTION

According to the particulars of the invention, the apparatus, designed for the purification of water possessing solvent waste content, includes a decanter-separator which provides for separation through decantation of undissolved solvent, a filtering element of microscopic porosity which absorbs the solvent from the water, a detection cell which receives the water from the filtering element and which includes an air inlet opening above the surface of the water and a solvent vapor detector located above the surface of the water.

According to a particular of the invention, if the solvent is heavier than water, the decanter-separator includes a main container with a long vertical axis; a delivery pipe located in the axis of the main container whose opening faces the bottom, this pipe being located slightly above the main container; a solvent recovery container which opens at the bottom of the main container, but whose cross section is smaller than that of the main container; a water discharge pipe which opens at the upper part of the main container.

According to another particular of the invention, the solvent recovery container is fitted with a detection system including an upper detection head and a lower detection head which are located inside the aforesaid solvent recovery container. An electro-valve is placed inside a lower orifice of the solvent recovery container and is controlled by the detection system as follows:

as the water/solvent separation surface reaches the level of the upper detection head, the electro-valve opens and lets the recovered solvent flow; as the water/solvent separation surface reaches the level of the lower detection head, the electro-valve closes.

In another version of the invention, if the solvent is lighter than water, the decanter-separator includes a singular container with a long vertical axis; a detection system incorporating an upper detection head and a lower detection head, respectively located one above the other inside the aforesaid singular container; a delivery pipe opening downward and below the level of the detection heads; a solvent discharge pipe which opens at the upper part of the singular container; a water discharge pipe which opens at the lower part of the singular container; an electro-valve inserted in the water discharge pipe and controlled by the detection system, closing as the water/solvent separation surface reaches the level of the lower detection head and reopening as the aforesaid separation surface reaches the level of the upper detection head.

According to another particular of the invention, the filtering element consists of a long central chamber surrounded by at least one tubular chamber, the water coming from the decanter-separator flowing consecutively through the length of all the chambers.

According to another particular of the invention, the material of microscopic porosity contained in the filtering element is made of granulated, activated carbon.

According to another particular of the invention, the filtering element is filled with a material of microscopic porosity, except for the portion of the element which is above the water circuit outlet which contains a purified fiberglass cartridge, designed to retain in suspension the particles escaping the material of microscopic porosity.

According to another particular of the invention, the detection cell includes a main container; a vertically oriented tube which crosses the aforesaid main container and includes a series of holes located below the upper water level in the main container, and close to that upper level; and air bubble generator located in the lower portion of the vertical tube; a solvent vapor detection head located in the upper portion of the vertical tube above the water level; a water inlet pipe originating in the filtering element and opening in the vertical tube below the bubble generator; a water discharge pipe which opens in the upper portion of the main container, acting as an overflow regulator to maintain the water level approximately constant; an air outlet pipe which opens in the upper portion of the vertical tube.

According to another particular of the invention, a small auxiliary filtering element, operating on the same principle as the aforesaid filtering element, is inserted in the water delivery pipe.

According to another particular of the invention, an intake orifice closed by a cock-valve is provided on the water inlet pipe to permit water sampling when checking system operation.

BRIEF DESCRIPTION OF THE DRAWINGS

The attached, schematic drawings provide a better understanding of the invention particulars.

DESCRIPTION OF THE PREFERRED EMBODIMENT

Figure 1:
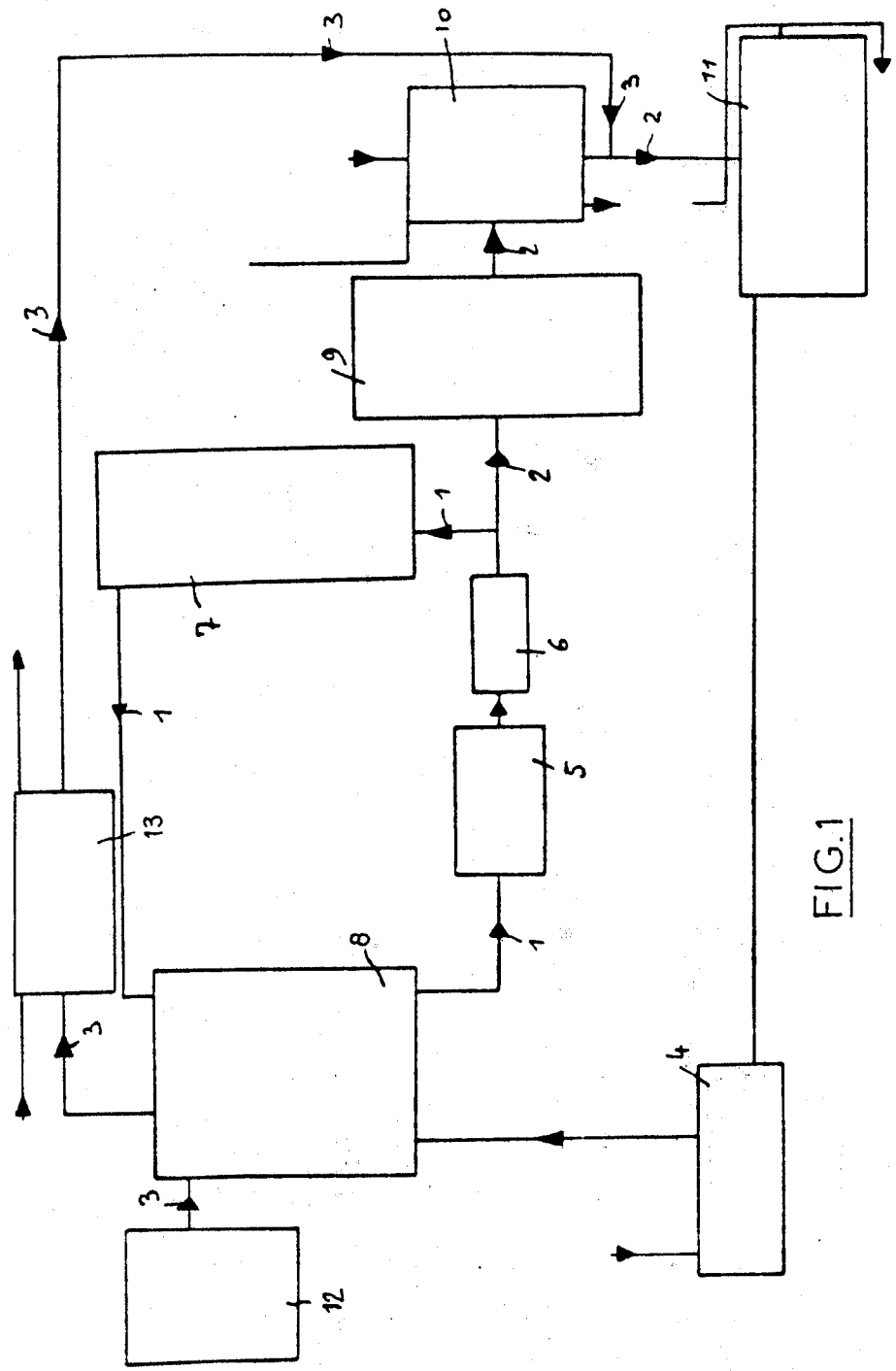
FIG. 1 is a schematic view illustrating the operation of a clothing degreasing machine.

FIG. 1 shows the operation of a clothing degreasing machine, perchlorethylene being the solvent generally used with this machine.

Usually, the operation during the cleaning cycle is continuous and does not lead to the discharge of solvent into the atmosphere or the sewer. The arrows 1 indicate the solvent flow: the solvent comes from tank 4, after injection into degreasing drum 8, successively flows through pin filter 5, pump 6, and powder filter 7 before returning to drum 8.

Upon completion of the cleaning process, 75% of the solvent remains in the clothes in drum 8, and 25% of the solvent is directly discharged into still 9 to undergo a regeneration cycle as illustrated by arrows 2. Distillation begins, consisting of the conversion of the water-solvent azeotrope to a pure state. The dissociation of the water molecules from the solvent molecules at the azeotrope stage occurs in condenser 10, and the separation, based on the principle of density difference, occurs in separator 11 of the machine.

The arrows 3 illustrate the clothes drying phase during which the air, heated at approximately 60° C., is blown into drum 8 by heating battery 12. The solvent laden air escapes from drum 8, flows through cooling battery 13, where the condensed solvent is directed to separator 11. After decantation, the water is discharged into the sewer. In one day, a half liter of solvent is thus discharged into the sewer. In order to diminish this pollution and to avoid an excessive solvent concentration in the water, the waste water is diluted in 80 to 100 liters of cooling water.

However, this method is insufficient in order to dissolve completely the half liter of discharged solvent, it should be diluted in approximately 5000 liters of pure water at 25° C.

Figure 2:
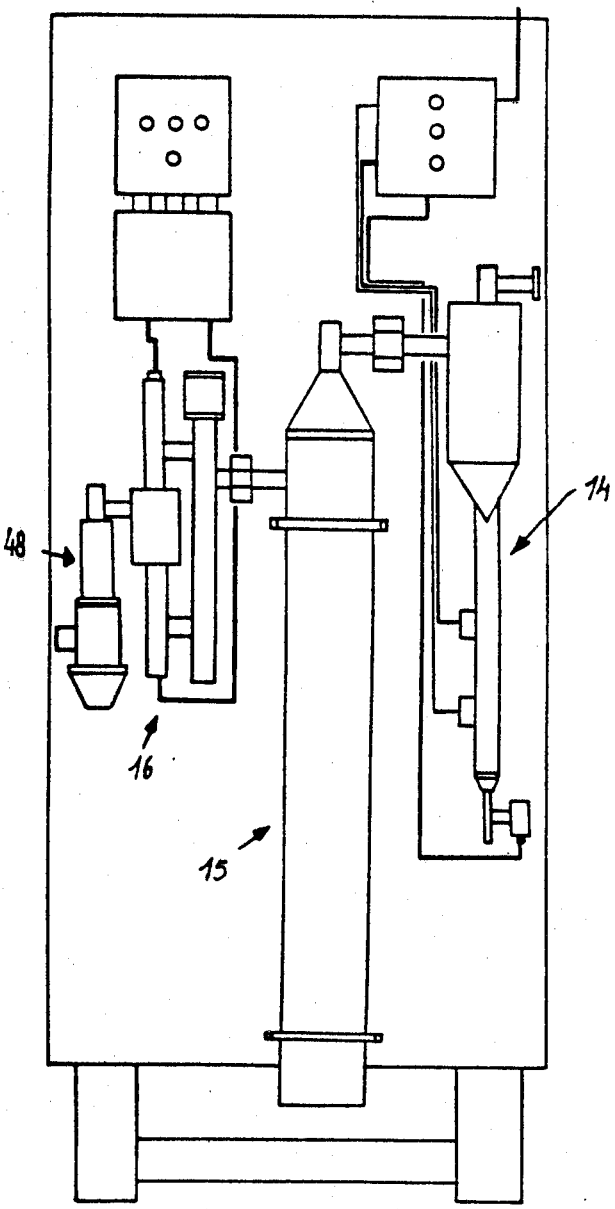
FIG. 2 is a general elevation view of an apparatus according to the invention.

The purification apparatus of the invention, in FIG. 2, consists of a decanter-separator 14, a main filtering element 15, and a detection cell 16.

This equipment is designed for the treatment of water containing a solvent heavier than water, such as perchlorethylene or trichlorethylene. But with a few modifications this apparatus can be used on solvents that are lighter than water.

Figure 3:
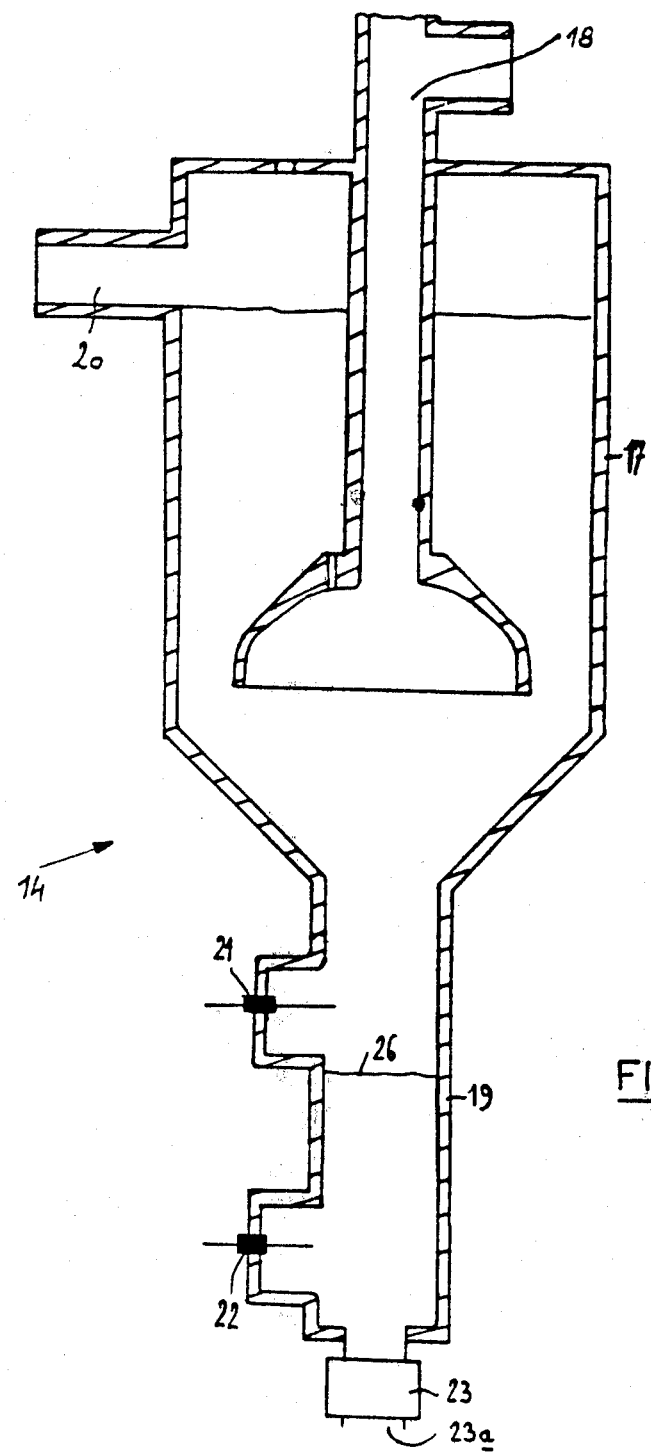
FIG. 3 is a section of the decanter-separator of that machine, along the vertical axis.

The decanter-separator 14, best illustrated in FIG. 3, includes a main container with a long vertical axis 17; an inlet pipe 18, laid along axis 17, of which the opening is directed downward and is located slightly above the lower end of container 17; a solvent recovery container 19 opening at the lower end of the main container and extending vertically above the main container 17—its cross section is smaller than that of container 17; a water discharge pipe 20 which opens at the upper end of container 17.

Container 19 is fitted with a detection system with upper detection head 21 and lower detection head 22, both situated inside container 19. The detection system controls electro-valve 23 which is positioned in a lower orifice 23a of container 19.

Figure 4:
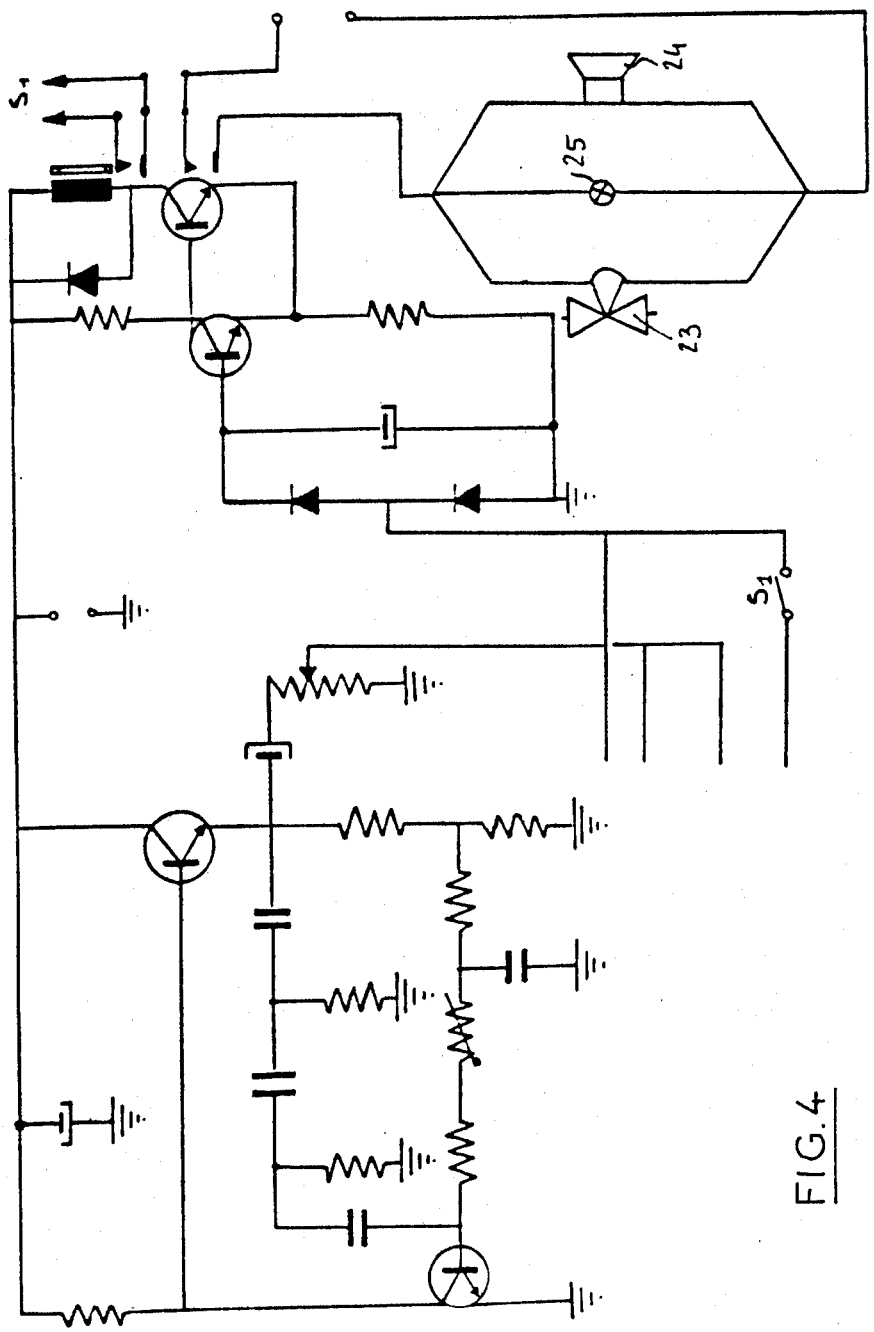
FIG. 4 is a diagram of the detection system fitted to the decanter-separator.

The electronic assembly of the detection system is illustrated in FIG. 4. The assembly includes an oscillating circuit delivering a voltage of approximately 2 volts A.C. 1000 Hz to the electrodes which constitute heads 21 and 22; a monitoring system for the minimum and maximum levels of the solvent, capable of simultaneously activating electro-valve 23, sound alarm 24 and warning light 25.

The decanter-separator 14 operates as follows:

It provides a physical decantation of the solvent, followed by a selective decantation which is controlled and monitored electronically.

As the water/solvent separation surface reaches or surpasses the level of upper head 21 the detection system opens electro-valve 23, whereupon the sound alarm 24 and the warning light 25 are activated. As the level 26 reaches lower head 22, electro-valve 23 closes, deactivating alarms 24 and 25.

The decanted solvent may then be returned to the still.

The spacing of detection heads 21 and 22 results in: increasing the solvent decantation time; avoiding undesired activation of electro-valve 23 upon arrival of chlorinated solvent drops; preventing the flow of saturated water through orifice 23a as it is drawn by the decanted solvent.

The low frequency, 1000 Hz, prevents polarization of the electrodes which constitute the heads 21 and 22.

Should incorrect operation of the degreasing machine cause an excessive flow of solvent in decanter-separator 14, alarms 24 and 25 will be activated to alert the operator.

Figure 5:
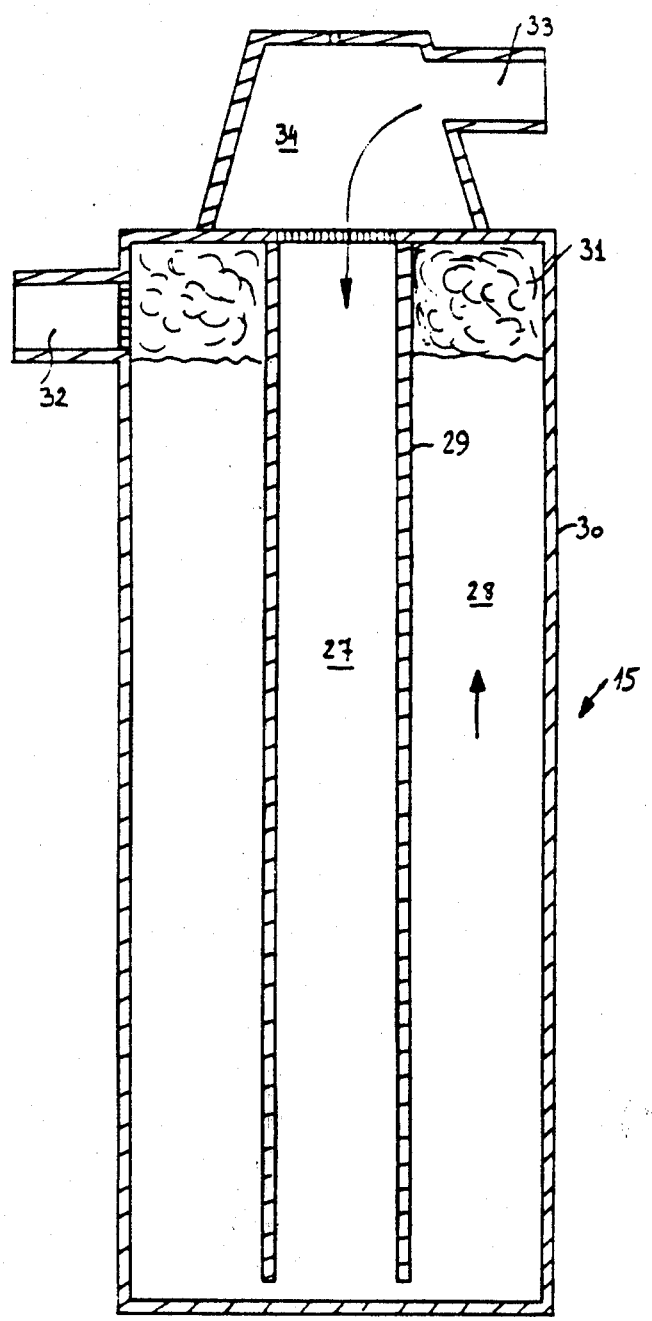
FIG. 5 is a section of the main filtering element of the machine, along the vertical axis.

The main filtering element 15 is best illustrated in FIG. 5. This element includes a long central chamber 27 surrounded by tubular chamber 28, both chambers encompassed by tubular wall 29, located inside cylindrical container 30. Chambers 27 and 28 are filled with activated granulated carbon. The upper end of chamber 28 contains a fiberglass cartridge 31 at the level of outlet orifice 32. Inlet orifice 33, located in the upper portion of chamber 27, opens in buffer reservoir 34, which is connected to pipe 20. The capacity of buffer reservoir 34 is equal to the volume included between two imaginary planes located respectively at the levels of heads 21 and 22 in container 19 of decanter-separator 14 (Refer to FIG. 3).

The main filtering element 15 operates in the following manner:

After flowing from decanter-separator 14 through pipe 20, the solvent saturated water is gravity fed to filtering element 15. Buffer reservoir 34 is used for the recovery of the saturated water upon arrival of an excessive quantity of chlorinated solvent in decanter-separator 14. The saturated water flows through chamber 27 from top to bottom, then through chamber 28 from bottom to top.

The activated, granulated carbon is a material of microscopic porosity, capable of absorbing solvent dissolved in the water. Fiberglass cartridge 31 prevents the passage of carbon particles suspended in the water. The activated carbon is constantly immersed in order to prevent vaporization.

To increase the service life of the filter it is possible to include a greater number of concentric compartments, increasing the passage time of the solvent saturated water through the filtering element.

Figure 6:
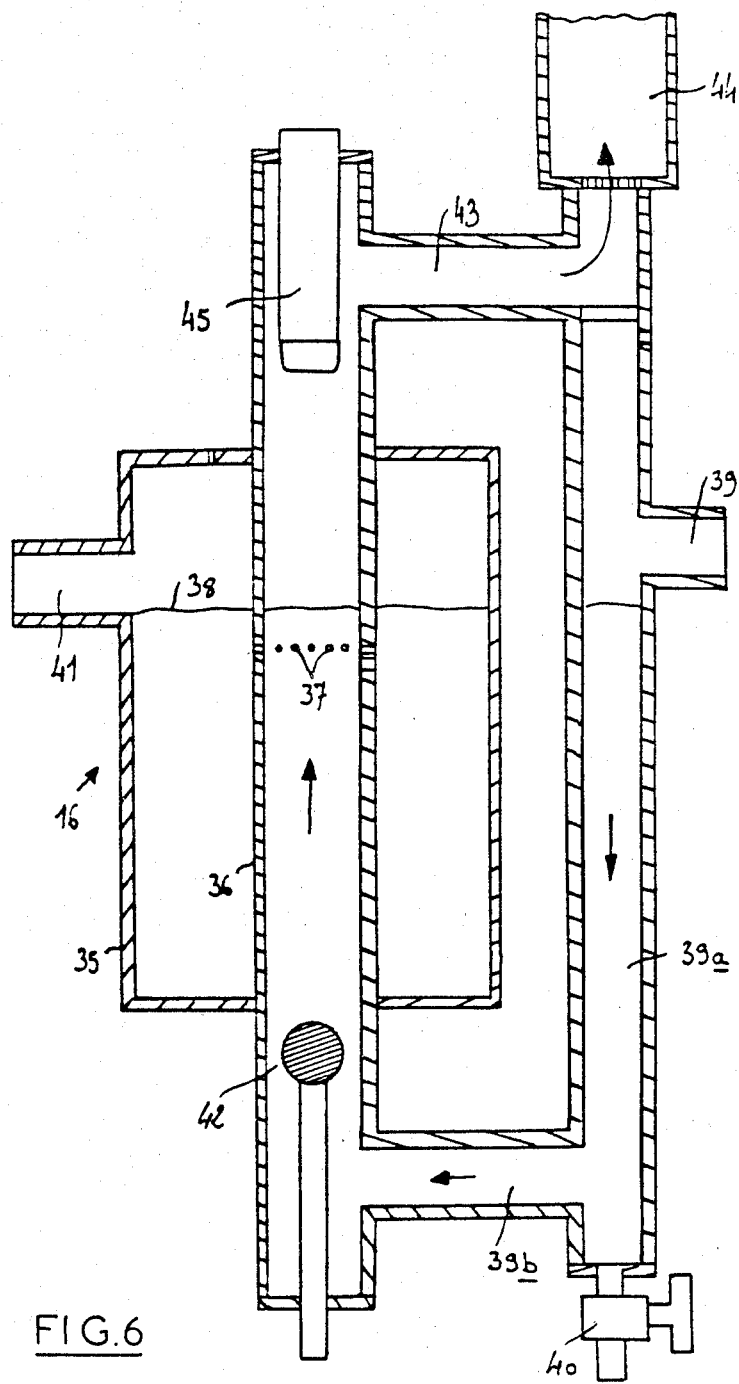
FIG. 6 is a section of the detection cell of the machine along the vertical axis.

Detection cell 16 is best illustrated in FIG. 6. This cell consists of a main container 35, vertically crossed by tube 36 which includes a series of holes 37 below the water surface 38 in container 35. Inlet pipe 39, connected to outlet 32 of main filtering element 15, opens in the lower portion of tube 36. Outlet orifice 32 is located above the level of the water surface 38. Pipe 39 includes vertical part 39a connected by an elbow pipe with sampling drain cock-valve 40 to horizontal member 39b. Water discharge pipe 41 opens in the upper portion of container 35 and operates as an overflow regulator to maintain the water surface 38 at an approximately constant level. Air bubble generator 42 is provided in the lower portion of tube 36. This bubble generator is fed by a low pressure air system and is made of a porous substance such as fritted glass. Air discharge pipe 43 opens in the upper portion of tube 36. A small filter 44, containing activated, granulated carbon is inserted in the pipe through which air is discharged into the external atmosphere. Solvent vapor detection head 45 is located in the upper portion of tube 36, above the water level 38. Head 45 is of a common type: it can be an iron oxide base component whose dielectric characteristic varies relative to the absorption of solvent.

Figure 7:
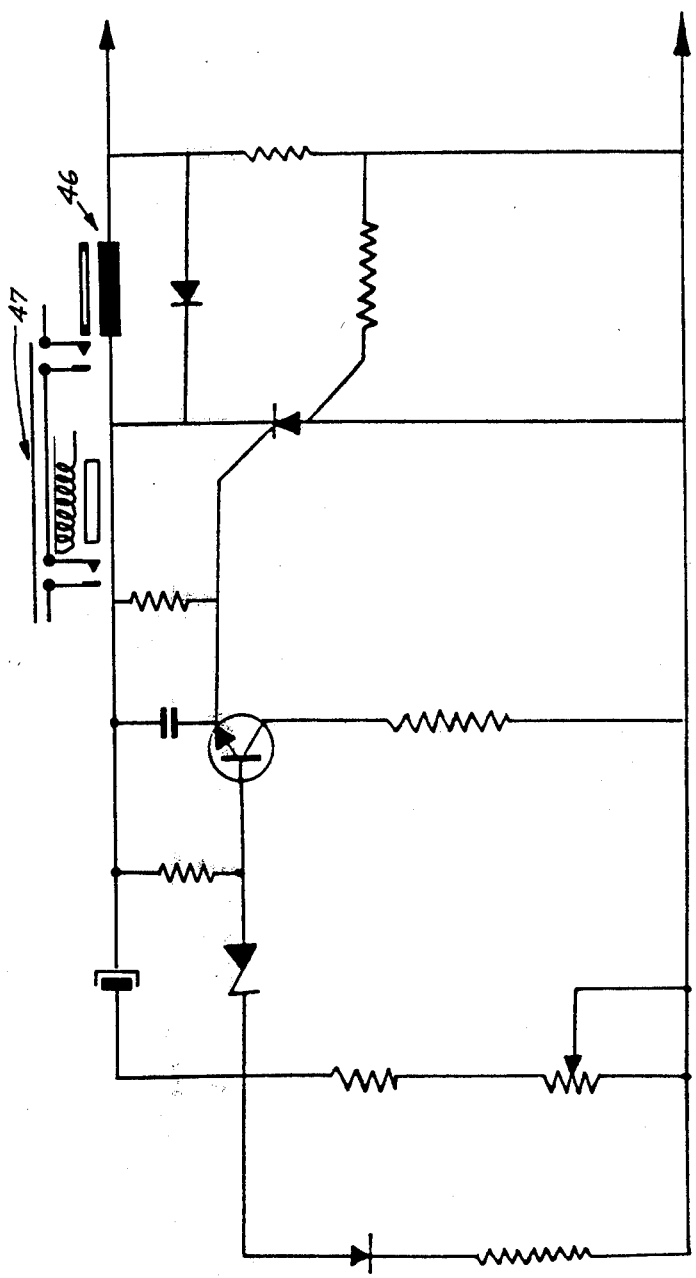
FIG. 7 is a diagram of the detection system.

Detection head 45 is connected to an electronic circuit controlling the activation of visual and sound alarms through relays 46 and 47 (FIG. 7). Relay 46 is activated as soon as detection head 45 absorbs solvent. Relay 47 is connected to a time-delay system which delays the closing of relay 47 with relation to relay 46 in excess of the stabilization time of detection head 45. The visual and sound alarms are activated only upon simultaneous stimulation of the coils of relays 46 and 47.

Detection cell 16 operates as follows:

As the activated carbon of the filtering element becomes saturated with solvent, the evaporation of the solvent dissolved in the water at the outlet of the main filtering element 15 is accelerated in tube 36 by injection of air bubbles produced by generator 42. Upon detection of solvent in the air recovered in the upper portion of tube 36, detection head 45 activates the visual and sound alarms. During its thermic stabilization, detection head 45 reacts as if solvent was present. The aforesaid time-delay system eliminates this problem. The small, activated carbon filter 44 prevents any discharge of solvent in the room where the apparatus is located.

Sampling drain cock-valve 40 enables inspectors to take water samples for chemical analysis and to verify the correct operation of the apparatus.

An auxiliary filtering element 48 is connected to discharge pipe 41 of detection cell 16 (FIGS. 2 and 6), so that the water flows through element 48 before being discharged into the sewer. This element has the same design as main filtering element 15 (FIG. 5), but is smaller. Element 48 eliminates all risk of contaminated waste water being discharged into the sewer. The alarms activated by detection head 45 do not require immediate replacement of main filtering element 15, thereby permitting the completion of the cleaning process. It is necessary to replace filtering elements 15 and 48 after the cleaning process is completed.

It is desirable to keep a supply of new filtering elements ready for replacement of used filtering elements, and, thereby avoid interruption of cleaning operations.

Used filtering elements may be recovered eventually by an authorized agency. Several ways of recovery are possible, such as thermic regeneration accomplished by vacuum oven treatment and providing for the recovery of the absorbed solvent, or regeneration with water vapor whereby the creation of an azeotrope permits the recovery of absorbed solvent, or even chemical regeneration.

The described apparatus requires little space and can be installed in any existing shop without special preparation or excavation. Its operation is economical, the only power usage being the electrical supply to the electronic circuits. The water is gravity fed throughout the apparatus.

The apparatus prevents the flow of raw solvent and of solvent saturated water into the sewer. In a cleaning shop, this apparatus creates an annual saving of approximately one hundred liters of solvent.

This apparatus improves the working conditions of sewer personnel and of degreasing machine operators, even in case of accidental misuse. It protects water treatment facilities against pollution.

This apparatus can be used for the treatment of solvents not miscible in water and whose density exceeds 1, and which are not conductive and are absorbed by activated carbon, such as trichlorethylene, perchlorethylene, carbon tetrachloride, trichloro 1-1-1 ethane, chloroform, and carbon sulfide.

With modification the apparatus can be used for the treatment of solvents whose density is lower than 1. In such case the decanter-separator 14 should be designed as shown in FIG. 8 and include: a singular container with a long, vertical axis; a detection system having an upper detection head 50 and a lower detection head 51, located one above the other inside container 49 and below water level 52; an inlet pipe 53 whose opening faces down and is located below heads 50 and 51; a solvent discharge pipe 55, which opens in the upper portion of container 49 above water level 52; a water discharge pipe 54 which opens in the lower and upper portions of container 49 above pipe 55; an electro-valve 56 inserted in pipe 54, and controlled by the detection system, which closes when water/solvent separation surface 57 falls to the level of lower head 51 and opens when the separation surface 57 rises to upper head 50.

Figure 8:
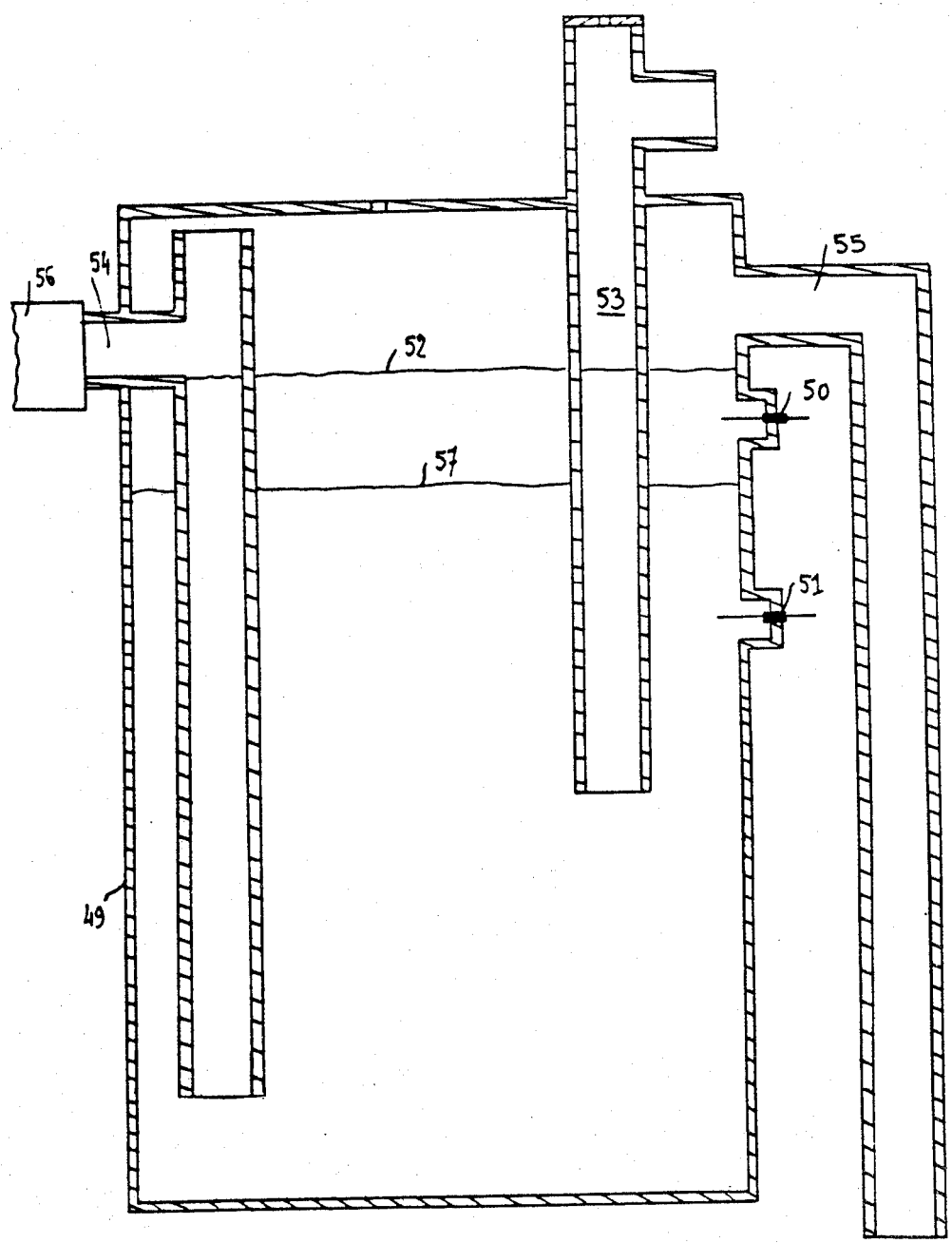
FIG. 8 illustrates another version of the decanter-separator according to a variation of the invention.

The apparatus, equipped with a decanter-separator, and illustrated in FIG. 8, is used for the treatment of solvents not miscible in water and having a density lower than 1, and which are non-conductive and are absorbed by activated carbon, such as: pentane, hexane, heptane, octane, nonane, decane, amylacetate, butylacetate and cyclohexane.

Having described the invention, I claim:

1. An apparatus for the purification of a water solution possessing miscible and nonmiscible solvent, said apparatus comprising:

a decanter-separator means for separating by decantation said nonmiscible solvent from said water solution;

a main filtering element mounted downstream of said decanter-separator means for receiving gravity fed miscible solvent from said decanter-separator means, said main filtering element further having a filter housing having at least two chambers, an inlet mounted to one of said at least two chambers for receiving said miscible solvent from said decanter-separator means; an outlet mounted to another of said at least two chambers to discharging said filtered water solution; and means for detecting solvent vapor mounted downstream of said main filtering element, said detection means comprising:

an outlet;

an inlet located above said outlet;

water storage means interposed said inlet and said outlet, said storage means receiving gravity fed discharged water from said filtering element through said inlet of the detection means;

a source of air located in said storage means below the water level of said discharge water; and a detection cell mounted in said water storage means above the water level of said discharge water, such that, as the water solution enters the inlet of said detection means, the solution is gravity fed to said water storage means and said air of said air source is bubbled through said water solution to generate a solvent vapor which passes by said detection cell mounted above said water level in said water storage means whereby said solvent in said water storage means is monitered.

2. The apparatus as claimed in claim 1 wherein said decanter-separator means further comprises:

a main container having a first outlet means at one end, a second outlet at the opposite end and an inlet mounted to said opposite end terminating between said first outlet portion and said second outlet; said main container further having a vertical axis, said inlet further being positioned along said vertical axis of the main container and pointing towards said first outlet means at said one end such that when said solvent in said water solution is heavier than water, said nonmiscible solvent settles to said one end of said main container and said solvent saturated water solution discharges through said second outlet at the opposite end of the container.

3. The apparatus as claimed in claim 1 wherein said decanter-separator means further comprises:

a singular container having one end and an opposite end;

an inlet pipe mounted in said one end, said inlet pipe having a discharge end pointing towards said opposite end of the container;

means for detecting solvent levels mounted in said one end of the container, said detecting means further comprising a lower detection head mounted in a side wall of said container and an upper detection head mounted above said lower detection head;

said discharge end of the inlet pipe further being located below said lower detection head;

a solvent discharge pipe connected to said one end of the container above said upper detection head;

means for discharging water mounted to said container, said water discharge means comprising:

a discharge pipe having one end extending into said opposite end of the container;

an opposite end leading outside of said container; and valve means inserted in said discharge pipe responsive to said detection means such that as the nonmiscible solution containing solvent enters said container through said inlet pipe, the nonmiscible solvent rises to the top of said solution in said container, said valve means closing said water discharge pipe upon said container solution level dropping to the level of the lower detection head and whereby said valve means opens said water discharge pipe when the solution level in said container rises to the level of said upper detection head.

4. The apparatus as claimed in claim 2 wherein said outlet means further comprises:

an upper detection head mounted in said one end of the main container;

a lower detection head mounted in said one end in spaced relationship below said upper detection head, said upper and lower detection head further having means for detecting the level of said nonmiscible solvent in said main container;

a discharge pipe having one end in said one end of the container and an opposite end extending outside of said main container; and valve means mounted in said discharge pipe such that when the level of said nonmiscible solvent reaches said upper detection head, said valve means opens said discharge pipe to discharge said nonmiscible solvent from said main container and such that when the level of said nonmiscible solvent falls to the level of said lower detection head, said valve means closes said discharge pipe, said discharged nonmiscible solvent having a predetermined volume of discharge.

5. An apparatus as claimed in claim 1 wherein said at least two chambers comprise a central chamber having an inlet at one end communicating with the inlet of said main filtering element and an outlet at the opposite; a tubular chamber having an outlet at one end and an inlet at an opposite end, said tubular chamber surrounding said central chambers, said inlet of the tubular chamber communicating with said outlet of the central such that miscible solvent entering said inlet of the central chamber flows through said central chamber thence to said outlet of the central chamber; thence to the inlet of said tubular chamber; thence through said tubular chamber through said outlet of the tubular chamber and to said outlet of the main filtering element.

6. The apparatus as claimed in claim 5 wherein said central and tubular chambers have a filter media of microscopic porosity therein; and wherein further a purified fiberglass cartridge is interposed said tubular chamber outlet and said outlet of the main filtering element.

7. The apparatus as claimed in claim 4 wherein said main filtering element further comprises a buffer reservoir mounted to said filter housing upstream of said inlet of said at least one of said two chambers, said buffer reservoir receiving miscible solvent from said decanter-separator means, said buffer reservoir having a volume equal to the volume of said predetermined volume of nonmiscible solvent discharged.

8. The apparatus as claimed in claim 6 wherein said filter media is an activated granulated carbon.

9. The apparatus as claimed in claim 1 wherein said detection cell further comprises:

a vertical tube mounted in said water storage means, said vertical tube having a series of holes near the surface of the discharge water in said water storage means;

a vapor detection head located in the upper portion of said vertical tube above the water level;

a water inlet pipe opening in the bottom of the vertical tube, said water inlet pipe being connected to said inlet of said detection means;

said source of air being mounted in said vertical tube above said water pipe inlet and below said series of holes in the vertical pipe;

a water discharge pipe connected to said outlet of said detection means, said water discharge pipe acting as an overflow regulator to maintain the water surface level of said water storage container at a predetermined constant level; and an air discharge pipe connected to the upper portion of the vertical tube for discharging bubbled air in said vertical tube to the atmosphere.

10. The apparatus as claimed in claim 9 further comprising an auxiliary filtering element having an inlet communicating with the outlet of said detection means for receiving the discharged water therefrom and an outlet at the opposite end thereof with a filter media mounted therebetween.

11. The apparatus as claimed in claim 1 further comprising a means for discharging water in said water storage means for sampling thereof.

* * * * *

UNITED STATES PATENT OFFICE
CERTIFICATE OF CORRECTION

Patent No. 4,248,710  Dated February 3, 1981

Inventor(s) Jack Rampignon

It is certified that error appears in the above-identified patent and that said Letters Patent are hereby corrected as shown below:

Column 1, line 10, delete the words "Description of the Prior Art" and insert ----Background of the Invention----.

Column 3, line 25, after the word "into" insert ----the----.

Column 3, line 30, after the word "in" insert ----the----.

Column 3, line 32, before the word "separator" insert ----the----.

Column 4, line 9, after the word "activating" insert ----the----. Same line, after the numeral "23" insert ----the----.

Column 4, line 10, before the word "warning" insert ----the----.

Column 4, line 19, after the numeral "22" insert ----the----. Same line, after the word "closes" insert ----thereby----.

Column 4, line 26, delete the word "preventing" and insert ----prevents----.

Column 4, line 32, after the word "in" insert ----the----.

UNITED STATES PATENT OFFICE
CERTIFICATE OF CORRECTION

Patent No. 4,248,710     Dated   February 3, 1981

Inventor(s)  Jack Rampignon

It is certified that error appears in the above-identified patent and that said Letters Patent are hereby corrected as shown below:

Column 4, line 33, after the numeral "14" insert ----the----.

Column 4, line 65, after the word "filter" insert ----,----.

Column 5, line 66, delete the word "ways" and insert ----types----.

Column 8, line 34, after the word "chamber" insert ----,----.

Column 8, line 35, after the word "chamber" delete ";" and insert ----,----.

Column 8, line 36, after the word "chamber" first occurrence, delete the ";" and insert ----,----. Same line, after the word "chamber" second occurrence, insert ----,----.

Signed and Sealed this

*Thirtieth* Day of *June 1981*

[SEAL]

*Attest:*

*Attesting Officer*

RENE D. TEGTMEYER

*Acting Commissioner of Patents and Trademarks*